(12) United States Patent
Burne et al.

(10) Patent No.: US 7,001,775 B1
(45) Date of Patent: Feb. 21, 2006

(54) ASSAYS FOR AUTOANTIBODIES

(75) Inventors: Peter John Burne, Cardiff (GB); Bernard Rees Smith, Cardiff (GB)

(73) Assignee: RSR Limited, Cardiff (GB)

(*) Notice: Subject to any disclaimer, the term of this patent is extended or adjusted under 35 U.S.C. 154(b) by 0 days.

(21) Appl. No.: 09/582,524

(22) PCT Filed: Oct. 27, 1999

(86) PCT No.: PCT/GB99/03548

§ 371 (c)(1),
(2), (4) Date: Jun. 27, 2000

(87) PCT Pub. No.: WO00/25137

PCT Pub. Date: May 4, 2000

(30) Foreign Application Priority Data

Oct. 27, 1998 (GB) .................................... 9823397

(51) Int. Cl.
*G01N 33/543* (2006.01)
(52) U.S. Cl. .................. 436/518; 435/7.1; 435/7.9; 435/7.92; 435/7.93; 435/7.94; 435/7.95; 435/810; 435/971; 435/973; 435/975; 436/164; 436/172; 436/506; 436/524; 436/528; 436/536; 436/548; 436/805; 436/815; 436/824
(58) Field of Classification Search .............. 435/28, 435/4, 7.1, 7.9, 7.92–7.95, 810, 971, 973, 435/975; 436/503, 506, 518, 548, 164, 172, 436/524, 528, 536, 805, 815, 824
See application file for complete search history.

(56) References Cited

U.S. PATENT DOCUMENTS

| 3,654,090 | A |   | 4/1972  | Schuurs et al. |         |
|-----------|---|---|---------|----------------|---------|
| 4,281,061 | A | * | 7/1981  | Zuk et al.     | 435/7   |
| 4,343,896 | A | * | 8/1982  | Wolters et al. | 435/7   |
| 4,444,879 | A | * | 4/1984  | Foster et al.  | 435/7   |
| 4,486,530 | A | * | 12/1984 | David et al.   | 435/7   |
| 4,690,907 | A |   | 9/1987  | Hibino et al.  |         |
| 4,861,711 | A |   | 8/1989  | Friesen et al. | 436/7   |
| 5,077,198 | A | * | 12/1991 | Shih           | 435/7.9 |
| 5,120,643 | A | * | 6/1992  | Ching et al.   | 435/7.92|

(Continued)

FOREIGN PATENT DOCUMENTS

EP  0 183 442  6/1986

(Continued)

OTHER PUBLICATIONS

Janeway et al The immune Sytem in Health and disease Immunobiology 3 rd 1997.*

(Continued)

*Primary Examiner*—Christopher L. Chin
(74) *Attorney, Agent, or Firm*—Merchant & Gould P.C.

(57) ABSTRACT

A method and kit for screening a sample of body fluid for at least one autoantibody to at least one antigen. A source of at least one antigen to the autoantibody is provided. A substrate having immobilized thereto at least one antibody to the antigen is also provided. The antigen source is contacted with the sample of body fluid, so as to obtain a mixture wherein the antigen is allowed to substantially bind with the autoantibody, when the latter is present in the sample of body fluid. The mixture is allowed to flow relative to the substrate so as to allow the mixture to contact the antibody immobilized to the substrate. Labeling means are provided to permit monitoring of binding of the autoanitbody and the antigen present in the mixture, so as to provide an indication of the presence of the autoanitbody in the sample of body fluid.

28 Claims, 5 Drawing Sheets

U.S. PATENT DOCUMENTS 5,206,177 A * 4/1993 Delacroix et al. .......... 436/518
5,229,073 A * 7/1993 Luo et al. ..................... 422/56
5,501,955 A * 3/1996 Bergman .................... 435/7.93
5,622,871 A * 4/1997 May et al. .................. 436/514
5,814,461 A   9/1998 Bergmann et al.

FOREIGN PATENT DOCUMENTS

| EP | 0 186 799 | 7/1986 |
| EP | 0 225 054 | 6/1987 |
| EP | 0 719 858 A2 | 3/1996 |
| GB | 1 589 234 | 5/1981 |
| WO | PCT/US90/05066 | 9/1990 |
| WO | 9222797 * | 12/1992 |
| WO | PCT/US93/03837 | 4/1993 |
| WO | PCT/GB93/02454 | 11/1993 |
| WO | PCT/EP94/02748 | 8/1994 |
| WO | 9506258 * | 3/1995 ................. 33/74 |
| WO | WO 96/27129 | 9/1996 |
| WO | WO 96/27129 A1 * | 9/1996 |

OTHER PUBLICATIONS

Preissner et al Clin. Chem 34/9 1794-1798 (1988).*

Andonopoulos et al., "Thyroid Function and Immune Profile in Rheumatoid Arthritis. A Controlled Study", Clinical Rheumatology (1996); vol. 15, No. 6: 599-603.

Balazs et al., "Soluble Intercellular Adhesion Molecule-1 (sICAM-1) In Graves' Disease", Acta Microbiologica et Immunologica (1994); vol. 41, No. 4: 451-456.

* cited by examiner

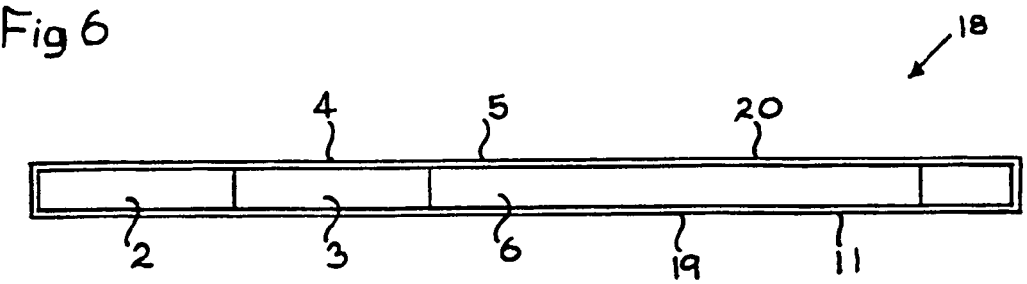
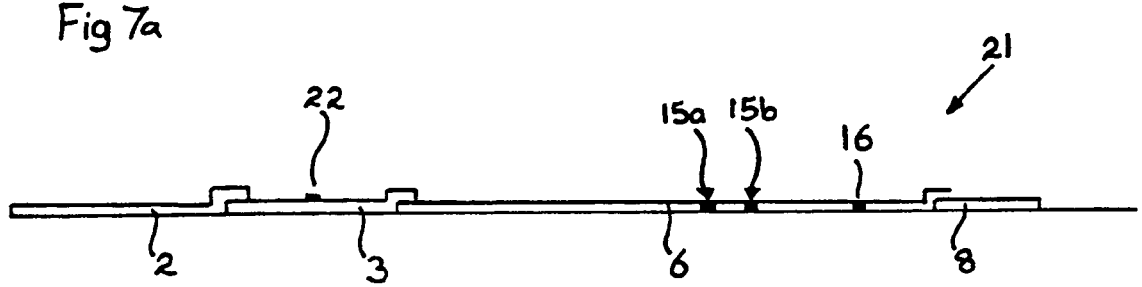
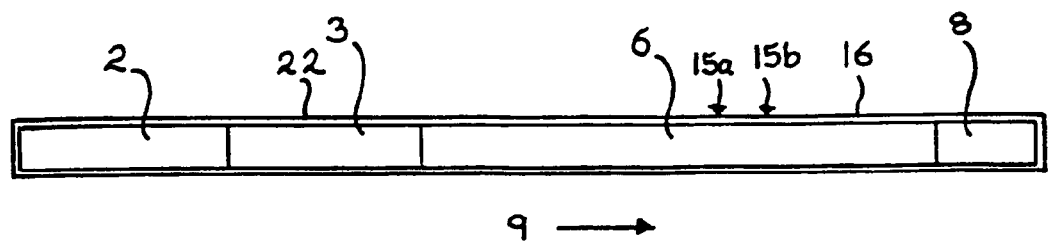

ASSAYS FOR AUTOANTIBODIES

CROSS REFERENCE TO RELATED APPLICATIONS

This application is a National Phase application concerning a filing under 35 U.S.C. 371, of International Patent Application Serial No. PCT/GB99/03548, filed Oct. 27, 1999, which claims priority on British Patent Application Serial No. 9823397.6, filed Oct. 27, 1998, both of which are incorporated herein by reference.

BACKGROUND OF THE INVENTION

1. Field of the Invention

The present invention is concerned with assays for screening a sample of body fluid for autoantibodies to various antigens. In particular, the present invention is concerned with screening a sample of body fluid for autoantibodies associated with autoimmune thyroid disease.

2. Description of Related Art

Autoimmune diseases are characterised by the presence of circulating autoantibodies and in autoimmune thyroid disease, for example, the autoantibodies are directed to three different thyroid proteins, namely thyroid peroxidase (TPO), thyroglobulin (Tg) and the receptor for thyroid stimulating hormone (TSHR).

In the absence of thyroid disease, thyroid function is controlled by a feedback system involving the pituitary gland. The pituitary secretes the hormone thyroid stimulating hormone (TSH) into the circulating blood. TSH then acts on TSH receptors (TSHR) on the surfaces of thyroid cells in such a way as to stimulate the synthesis and release of thyroid hormones (which stimulate metabolic processes in almost all cells). As circulating thyroid hormone levels rise these hormones act back on the pituitary to inhibit TSH release. This causes blood TSH levels to fall with the effect of lowering blood thyroid hormone levels. This feedback mechanism allows circulating thyroid hormone levels to be maintained within close limits, thus ensuring good control over metabolic activity.

In thyroid disease, however, the above feedback system is often distorted. For example, when the thyroid is under-active (hypothyroidism), thyroid hormone levels are lower than normal and because these low levels do not suppress TSH release, circulating TSH levels are high. In the case of thyroid over-activity (hyperthyroidism), thyroid levels are higher than normal and these high levels cause TSH release to be suppressed more than normal and circulating TSH levels are low.

Hypothyroidism is often caused by autoimmune attack on the thyroid and this attack is associated with the formation of autoantibodies to two different thyroid proteins (autoantigens), namely TPO and Tg. Screening for autoantibodies to TPO and/or autoantibodies to Tg is important in the diagnosis and management of the various forms of autoimmune hypothyroidism, including post-partum thyroiditis and the like. This screening for TPO autoantibodies and/or Tg autoantibodies (which indicates the likely cause of thyroid underactivity) complements monitoring of circulating TSH levels or thyroid hormone levels which reflect the extent of thyroid under-activity and effectiveness of treatment.

Hyperthyroidism is also often caused by autoimmune attack on the thyroid but in this condition, autoantibodies are formed to the TSHR. These TSHR autoantibodies mimic the effects of TSH and cause circulating thyroid hormone levels to be high. Such high thyroid hormone levels act on the pituitary and suppress circulating TSH levels and consequently TSH levels are lower than normal. Screening for autoantibodies to the TSHR is important in the diagnosis of autoimmune hyperthyroidism. As with autoimmune hypothyroidism, screening for TSHR autoantibodies complements monitoring of circulating TSH levels or thyroid hormone levels which reflect the extent of thyroid over-activity and effectiveness of treatment.

In patients with thyroid cancer, screening for circulating levels of Tg is often used as an indicator of the presence of any residual malignant thyroid tumour cells after treatment. Tg levels are usually measured by assays which depend on monoclonal and/or polyclonal antibodies to Tg but if autoantibodies to Tg are present in patient test samples, these autoantibodies can interfere with the Tg assays, giving erroneous results. Consequently, screening for autoantibodies to Tg is often carried out at the same time as detection and monitoring of circulating Tg levels.

Many examples of other (i.e. non thyroid) autoimmune diseases are known, such as type 1 diabetes (where autoantibodies are formed to insulin, glutamic acid decarboxylase and to the islet cell protein ICA512 or IA2), celiac disease (where autoantibodies are formed to tissue transglutaminase), myasthenia gravis (where autoantibodies are formed to the acetylcholine receptor and to calcium channels), systemic lupus erythematosus (where autoantibodies are formed to DNA and to various nuclear proteins), and the like.

Currently, several types of assay have been used to measure autoantibodies. These include methods using, for example, radioactive labels in which the labelled antigen binds directly to the respective autoantibody, or methods using radioactive labels in competition assays. Several non-radioactive assays have also been used, including those based on agglutination of particles coated with antigen. In addition, sandwich type enzyme linked immunosorbent assays (ELISA) are available. These sandwich type enzyme linked immunosorbent assays have used ELISA plates coated with antigen in combination with an anti-human IgG reagent conjugated with an enzyme such as horseradish peroxidase.

However, there have been some major limitations associated with current assay methods for autoantibodies, for example:— the current assays can only be carried out away from the patient in specially equipped laboratories; and the current assays can only be carried out by experienced personnel and take several hours to complete.

It is therefore the aim of the present invention to provide an improved assay system which alleviates some of the aforementioned problems.

It is a further object of the present invention to provide simple and rapid assay methods for the monitoring of autoantibodies and also to provide diagnostic kits for use in the simple and rapid detection of autoantibodies for the diagnosis of autoimmune diseases. It is a further object of the present invention to provide an assay method that can be carried out near the point of patient care by personnel who do not have experience in laboratory procedures.

SUMMARY OF THE INVENTION

According to the present invention, therefore, there is provided a method of screening a sample of body fluid for at least one autoantibody to at least one antigen, which method comprises:

(a) providing a source of said at least one antigen to said autoantibody;

(b) providing a substrate having immobilised thereto at least one antibody to said antigen of step (a);

(c) contacting said antigen source of step (a) with said sample of body fluid, so as to obtain a mixture wherein said antigen is allowed to substantially bind with said autoantibody, when the latter is present in said sample;

(d) allowing said mixture obtained in step (c) to flow relative to said substrate of step (b) so as to allow said mixture to contact said antibody immobilised to said substrate;

(e) providing labelling means so as to permit monitoring of binding of said autoantibody and said antigen present in said mixture obtained in step (c); and (f) monitoring said binding so as to provide an indication of the presence of said autoantibody in said sample of body fluid.

A method according to the present invention is particularly suitable for use in screening for at least one autoantibody associated with autoimmune thyroid disease and where the antigen comprises a thyroid protein. Advantageously the thyroid protein is selected from the group consisting of thyroid peroxidase (TPO) thyroglobulin (Tg) and thyroid stimulating hormone receptor (TSHR), and even more advantageously the thyroid protein is selected from the group consisting of TPO and Tg.

According to a particularly preferred aspect of the present invention there is provided a method of screening a sample of body fluid for at least one autoantibody to at least one antigen comprising a thyroid protein selected from the group consisting of TPO, Tg and TSHR, which method comprises:

(a) providing a source of said at least one antigen to said autoantibody;

(b) providing a substrate having immobilised thereto at least one antibody to said antigen of step (a);

(c) contacting said antigen source of step (a) with said sample of body fluid, so as to obtain a mixture wherein said antigen is allowed to substantially bind with said autoantibody, when the latter is present in said sample;

(d) allowing said mixture obtained in step (c) to flow relative to said substrate of step (b) so as to allow said mixture to contact said antibody immobilised to said substrate;

(e) providing labelling means so as to permit monitoring of binding of said autoantibody and said antigen present in said mixture obtained in step (c); and (f) monitoring said binding so as to provide an indication of the presence of said autoantibody in said sample of body fluid.

A method according to the present invention preferably further comprises screening, in addition to the autoantibody screening, for at least one further biological marker present in a sample of body fluid from a patient, which marker is indicative of an autoimmune (typically thyroid) disease. Suitable biological markers can be selected from the group consisting of thyroid stimulating hormone (TSH), thyroxine, tri-iodothyronine, thyroglobulin (Tg) and the like. A method according to the present invention, therefore, preferably further comprises screening for the presence of at least one of the group consisting of TSH, thyroxine, tri-iodothyronine, Tg and the like, in a sample of body fluid obtained from a patient being tested for an autoimmune thyroid disease.

Such screening for the presence of a further biological marker or markers, can in the case of at least thyroxine and/or tri-iodothyronine, comprise screening for total or free (circulating) thyroxine and/or total or free (circulating) tri-iodothyronine. It may be desirable for means for screening for the presence of such a further biological marker or markers to be provided to the substrate employed in the present invention. Alternatively, means for screening for the presence of such a further biological marker or markers may be provided remote from the substrate substantially as hereinbefore described and suitably such remote screening means can be provided by a separate kit.

A method according to the present invention is also suitable for use in screening for at least one autoantibody associated with non-thyroid autoimmune disease, such as autoantibodies associated with type 1 diabetes, celiac disease, myasthenia gravis, systemic lupus erythematosus and the like.

It is often preferred that a method according to the present invention further employs at least one substantially non-immobilised antibody to the antigen and preferably a method according to the present invention comprises contacting in step (c) the antigen source and the sample of body fluid with the at least one substantially non-immobilised antibody. The term "substantially non-immobilised antibody" as used herein denotes an antibody that when provided in the mixture obtained in step (c) can be allowed to flow relative to the substrate employed in the present invention.

Preferably monitoring in step (f) of a method according to the present invention comprises observing a calorimetric change dependent on the binding of the autoantibody and the antigen present in the mixture obtained by step (c) Suitably the labelling means can comprise a colorimetric label selected from the group consisting of colloidal gold, colloidal carbon, coloured latex, dyed polymers and the like. Preferably the calorimetric label comprises colloidal gold. Alternatively, the monitoring in step (f) can involve electronic monitoring, whereby a visible read-out can be obtained indicative of autoantibody and antigen binding.

In the case where a calorimetric label is employed substantially as described above, the labelling means can further comprise a linker by which the calorimetric label, such as colloidal gold, may be attached to the antigen and/or antibody to be labelled. For example, a suitable linker can include -biotin-antibiotin-, -biotin-strepavidin-(SA) or the like. The labelling means may be applied to an antigen and/or antibody to be labelled substantially remote from the substrate. Alternatively, the labelling means may be provided to the substrate and such labelling means may be applied to the antigen and/or antibody to be labelled when the antigen and/or antibody has also been provided to the substrate.

Advantageously monitoring in step (f) of a method according to the present invention can further comprise providing a positive control that is present in the presence or absence of the autoantibody or autoantibodies being screened.

For example, the positive control may comprise, attaching to the substrate, a capture reagent for a colorimetric label, such as colloidal gold or the like. Alternatively, the positive control may comprise attaching to the substrate at least one control antibody to the antigen, which control antibody binds to a site on the antigen distinct to a binding site thereof for the autoantibody or autoantibodies being screened. The control antibody is preferably attached to the substrate employed in a method according to the present invention at a location of the substrate downstream relative to the immobilised antibody. A further alternative positive control can comprise attaching to the substrate at least one control agent that can bind to the at least one substantially non-immobilised antibody. Suitably the control agent can be selected from the group consisting of anti-mouse IgG, anti-human IgG or the like, and is typically attached to the substrate downstream relative to the immobilised antibody.

Suitably, a method according to the present invention comprises allowing a mixture obtained in step (c) to flow along the substrate and interact with the antibody immobilised to the substrate. It is preferred that at least the sample of body fluid is contacted with an application zone of the substrate, which application zone is provided upstream on the substrate relative to the immobilised antibody, and wherein the mixture is allowed to flow from the application zone along the substrate so as to interact with the immobilised antibody.

Aptly, the application zone can include the source of the antigen of step (a), and the mixture in step (c) is obtained by contacting the sample of body fluid with the antigen of the application zone. In the case where at least one substantially non-immobilised antibody is employed in a method according to the present invention, the application zone can further include the non-immobilised antibody, and the mixture in step (c) can be obtained by contacting said sample of body fluid and the antigen with the non-immobilised antibody present in the application zone.

Alternatively, the mixture of step (c) can be provided by contacting the antigen source of step (a) and the sample of body fluid substantially remote from the substrate and said mixture is subsequently contacted with the application zone of the substrate. In the case where at least one substantially non-immobilised antibody is employed in a method according to the present invention, the antigen source of step (a), the sample of body fluid and the non-immobilised antibody are contacted substantially remote from the substrate so as to provide the mixture of step (c), and the mixture is subsequently contacted with the application zone of the substrate.

In a first screening method according to the present invention, the sample of body fluid is screened for one autoantibody. Preferably the antigen includes a binding site to which either the autoantibody or the immobilised antibody can bind, whereby in step (d) binding of the immobilised antibody to the binding site is substantially precluded where the autoantibody has substantially bound to the binding site in step (c).

In a second screening method according to the present invention, the sample of body fluid is screened for at least first and second autoantibodies to the antigen, wherein at least first and second antibodies to the antigen are immobilised to the substrate in step (b). Preferably, the antigen includes:

a first binding site to which either the first autoantibody or the first immobilised antibody can bind, whereby in step (d) binding of the first immobilised antibody to the first binding site is substantially precluded where the first autoantibody has substantially bound to the first binding site in step (c); and a second binding site to which either the second autoantibody or the second immobilised antibody can bind, whereby in step (d) binding of the second immobilised antibody to the second binding site is substantially precluded where the second autoantibody has substantially bound to the second binding site in step (c);

wherein the first and second binding sites are substantially distinct sites on the antigen.

Labelling means can suitably be provided to the antigen in first or second screening methods substantially as described above. Alternatively, where at least one substantially non-immobilised antibody is employed in first or second screening methods according to the present invention, the non-immobilised antibody can be provided with the labelling means, where the non-immobilised antibody is capable of binding to a site on the antigen substantially distinct from a binding site for either (i) the autoantibody or autoantibodies being screened or (ii) the immobilised antibody, whereby in step (d), antigen is allowed to be substantially bound both to the immobilised antibody and to the non-immobilised antibody.

In a third screening method according to the present invention for screening the sample of body fluid for at least first and second autoantibodies to the antigen, and where at least one substantially non-immobilised antibody is employed, the non-immobilised antibody is capable of binding to a site on the antigen to which either the first or second autoantibody can bind and which is substantially distinct to a binding site on the antigen for the immobilised antibody, whereby in step (d) antigen is allowed to be substantially bound both to the immobilised antibody and to the non-immobilised antibody.

In the third screening method according to the present invention, the antigen preferably includes:

a first binding site to which either the first autoantibody or the immobilised antibody can bind, whereby in step (d) binding of immobilised antibody to the first binding site is substantially precluded where the first autoantibody has substantially bound to the first binding site in step (c); and a second binding site to which either the second autoantibody or the non-immobilised antibody can bind;

wherein the first and second binding sites are substantially distinct sites on the antigen.

In the third screening method according to the present invention, preferably the non-immobilised antibody is provided with the labelling means. Suitably the immobilised antibody can comprise a first autoantibody to the antigen and the non-immobilised antibody can comprise a second autoantibody to the antigen.

The present invention further provides a kit for use in screening a sample of body fluid for at least one autoantibody to at least one antigen, which kit comprises:

(a) a source of the at least one antigen to the autoantibody;

(b) a substrate having immobilised thereto at least one antibody to the antigen;

(c) means for contacting the antigen source with the sample of body fluid, so as to obtain a mixture wherein the antigen is allowed to substantially bind with the autoantibody, when the latter is present in the sample;

(d) means for allowing the mixture to flow relative to the substrate so as to allow the mixture to contact the antibody immobilised to said substrate;

(e) labelling means to permit monitoring of binding of the autoantibody and the antigen present in the mixture; and (f) means for monitoring the binding so as to provide an indication of the presence of the autoantibody in the sample of body fluid.

Substantially as hereinbefore described with reference to a method of screening according to the present invention, a kit according to the present invention is particularly suitable for use in screening for at least one autoantibody associated with autoimmune (typically thyroid) disease and where the antigen comprises a thyroid protein. Advantageously the thyroid protein is selected from the group consisting of thyroid peroxidase (TPO), thyroglobulin (Tg) and thyroid stimulating hormone receptor (TSHR), and even more advantageously the thyroid protein is selected from the group consisting of TPO and Tg.

According to a preferred embodiment of the present invention there is provided a kit for use in screening a sample of body fluid for at least one autoantibody to at least one antigen comprising a thyroid protein selected from the group consisting of TPO, Tg and TSHR, which kit comprises:

(a) a source of the at least one antigen to the autoantibody;
(b) a substrate having immobilised thereto at least one antibody to the antigen;
(c) means for contacting the antigen source with the sample of body fluid, so as to obtain a mixture wherein the antigen is allowed to substantially bind with the autoantibody, when the latter is present in the sample;
(d) means for allowing the mixture to flow relative to the substrate so as to allow the mixture to contact the antibody immobilised to the substrate;
(e) labelling means to permit monitoring of binding of the autoantibody and the antigen present in the mixture; and
(f) means for monitoring the binding so as to provide an indication of the presence of the autoantibody in the sample of body fluid.

Substantially as hereinbefore described with reference to a method of screening according to the present invention a kit according to the present invention further comprises means for screening for at least one further biological marker present in patient, which marker is indicative of an autoimmune (typically thyroid) disease. Suitable biological markers can be selected from the group consisting of thyroid stimulating hormone (TSH), thyroxine, tri-iodothyronine, thyroglobulin (Tg) and the like. Preferably, therefore, a kit according to the present invention further comprises means for screening for the presence of at least one of TSH, thyroxine, tri-iodothyronine, Tg and the like in the sample of body fluid.

Suitably, a kit according to the present invention further comprises a source of at least one substantially non-immobilised antibody to the antigen substantially as hereinbefore described and means whereby the non-immobilised antibody can be contacted with the antigen source and the sample of body fluid.

Advantageously, the monitoring means employed in a kit according to the present invention comprise means for observing a calorimetric change dependent on the binding of the autoantibody and the antigen present in said mixture substantially as hereinbefore described, although other monitoring means can be employed also substantially as hereinbefore described. Suitably the labelling means can comprise a calorimetric label, such as colloidal gold substantially as hereinbefore described and a linker can be provided for attaching the calorimetric label to an antigen and/or antibody to be labelled again substantially as hereinbefore described. In the case where labelling means are applied to an antigen and/or antibody following application thereof to the substrate, the substrate may be provided with the labelling means for subsequent application.

Preferably the substrate of a kit according to the present invention can further comprise a positive control substantially as hereinbefore described with reference to a method according to the present invention.

Preferably the substrate of a kit according to the present invention can comprise an application zone provided upstream on the substrate relative to the immobilised antibody, whereby the mixture is allowed to flow from the application zone along the substrate so as to interact with the immobilised antibody.

Suitably, that application zone can include the source of the antigen, and the mixture is obtained by contacting the sample of body fluid with the antigen of the application zone. In the case where a kit according to the present invention further comprises at least one substantially non-immobilised antibody substantially as hereinbefore described, the application zone can further include the non-immobilised antibody, and means are provided whereby the mixture is obtained by contacting the sample of body fluid and the antigen with the non-immobilised antibody present in the application zone.

Alternatively, a kit according to the present invention can comprise means whereby the antigen source and the sample of body fluid are contacted substantially remote from the substrate so as to provide the mixture and means whereby the mixture is subsequently contacted with the application zone. In the case where a kit according to the present invention comprises at least one substantially non-immobilised antibody, means can be provided whereby the antigen source, the sample of body fluid and/or the non-immobilised antibody are contacted substantially remote from the substrate so as to provide the mixture, and means whereby the mixture is subsequently contacted with the application zone.

A kit according to the present invention preferably further comprises wick means arranged downstream relative to the immobilised antibody so as to permit or potentiate flow of at least the sample of body fluid towards the immobilised antibody.

A first kit according to the present invention is suitable for screening for one autoantibody in the sample of body fluid and the antigen includes a binding site to which either the autoantibody or the immobilised antibody can bind, whereby binding of the immobilised antibody to the binding site is substantially precluded where the autoantibody has previously substantially bound to the binding site.

A second kit according to the present invention is suitable for screening the sample of body fluid for at least first and second autoantibodies to the antigen, wherein at least first and second antibodies to the antigen are immobilised to the substrate. Preferably the antigen includes:

a first binding site to which either the first autoantibody or the first immobilised antibody can bind, whereby binding of the first immobilised antibody to the first binding site is substantially precluded where the first autoantibody has previously substantially bound to the first binding site; and a second binding site to which either the second autoantibody or the second immobilised antibody can bind, whereby binding of the second immobilised antibody to the second binding site is substantially precluded where the second autoantibody has previously substantially bound to the second binding site;

wherein the first and second binding sites are substantially distinct sites on the antigen.

Suitably the labelling means can be provided to the antigen of a first or second kit according to the present invention. Alternatively, where a first or second kit according to the present invention further comprises at least one substantially non-immobilised antibody, the non-immobilised antibody can be provided with the labelling means, which non-immobilised antibody is capable of binding to a site on the antigen substantially distinct from a binding site for either (i) the autoantibody or autoantibodies being screened or (ii) the immobilised antibody, whereby antigen is allowed to be substantially bound both to the immobilised antibody and to the non-immobilised antibody.

A third kit according to the present invention is suitable for screening the sample of body fluid for at least first and second autoantibodies to the antigen, which third kit further comprises at least one substantially non-immobilised antibody, wherein the non-immobilised antibody is capable of binding to a site on the antigen to which either the first or second autoantibody can bind and which is substantially distinct to a binding site on the antigen for the immobilised antibody, whereby antigen is allowed to be substantially bound both to the immobilised antibody and to the non-immobilised antibody.

Preferably the antigen of the third kit includes:
a first binding site to which either the first autoantibody or the immobilised antibody can bind, whereby binding of immobilised antibody to the first binding site is substantially precluded where the first autoantibody has previously substantially bound to the first binding site; and
a second binding site to which either the second autoantibody or the non-immobilised antibody can bind;

wherein the first and second binding sites are substantially distinct sites on the antigen.

Suitably the non-immobilised antibody is provided with the labelling means in a third kit according to the present invention. It may be preferred that the immobilised antibody comprises a first autoantibody to the antigen and the non-immobilised antibody comprises a second autoantibody to the antigen.

Non-immobilised and immobilised antibodies employed in methods or kits according to the present invention are generally provided in substantially purified form and can comprise monoclonal antibodies, polyclonal antibodies, recombinant antibodies, antibody fragments, synthetic antibodies, substances mimicking antibodies, autoantibodies or the like. Preferred aspects of the present invention comprise the non-immobilised antibody and/or the immobilised antibody comprising an autoantibody, which may preferably be a monoclonal antibody, and/or the non-immobilised antibody and/or the immobilised antibody can comprise a monoclonal antibody.

In first and second screening methods, and first and second kits, according to the present invention, in the presence of an autoantibody or autoantibodies being screened for in a sample of body fluid, generally binding of the autoantibody or autoantibodies with the antigen precludes binding of the latter with immobilised antibody. In the case where a calorimetric label is employed in first and second screening methods and kits according to the present invention, substantially no colour change due to binding of antigen to immobilised antibody is thus seen in the presence of an autoantibody or autoantibodies; alternatively in the absence of an autoantibody or autoantibodies, a colour change is seen due to binding of antigen to immobilised antibody.

In a third screening method and kit according to the present invention, again in the absence of autoantibody or autoantibodies being screened, a colour change is seen indicative of antigen and immobilised antibody binding. In the presence of autoantibody or autoantibodies, substantially no colour change can be seen, or some colour change can be seen due to non-immobilised antibody binding to antigen in competition with autoantibody and antigen binding whereby antigen bound to non-immobilised antibody can also bind to immobilised antibody giving a colour change.

Suitably an antigen employed in methods or kits of the present invention can comprise recombinant antigen, native antigen (autoantigen), synthetic antigen, antigen fragments, substances mimicking antigen or the like.

A substrate for use in the present invention can comprise a membrane of nitrocellulose, cellulose acetate, a polyamide or the like.

Generally the present invention comprises screening a sample of blood, plasma, serum or urine for at least one autoantibody.

The present invention further provides use of a kit substantially as hereinbefore described in screening a sample of body fluid for at least one autoantibody to at least one antigen again substantially as hereinbefore described.

There is still further provided by the present invention a method of screening a patient for at least one autoantibody to at least one antigen, which method comprises:
(a) obtaining a sample of body fluid from the patient;
(b) contacting the sample of body fluid of step (a) with an antigen source of a kit substantially as hereinbefore described so as to obtain a mixture wherein said antigen is allowed to substantially bind with the autoantibody, when the latter is present in the sample;
(c) allowing the mixture to flow relative to a substrate of the kit of step (b) so as to allow the mixture to contact the antibody immobilised to the substrate; and
(d) monitoring binding of the autoantibody and the antigen present in the mixture, so as to provide an indication of the presence of the autoantibody in the sample of body fluid from the patient.

A method substantially as described above is preferably for testing the patient for an autoimmune thyroid disease and may preferably further comprise screening for the presence of at least one of TSH, thyroxine, tri-iodothyronine and Tg in the sample of body fluid obtained form the patient substantially as hereinbefore described.

There is further provided by the present invention a method of treating a patient suffering from, or susceptible to, an autoimmune disease, which method comprises:
screening the patient for at least one autoantibody to at least one antigen substantially as hereinbefore described; and
when at least one autoantibody is detected in a sample of body fluid obtained from the patient at a level indicative of an autoimmune disease, administering to the patient at least one therapeutically active substance effective in the treatment of the autoimmune disease.

Substantially as hereinbefore described the autoimmune disease is a thyroid autoimmune disease and the therapeutically active substance comprises a pharmaceutical effective for treatment of thyroid autoimmune disease. The mode of administration, dose and the like is generally at the discretion of an attendant physician.

There is still further provided by the present invention, in combination, a kit substantially as hereinbefore described, and at least one therapeutically active substance effective for treatment of an autoimmune disease (typically a thyroid autoimmune disease) substantially as hereinbefore described.

BRIEF DESCRIPTION OF THE DRAWINGS

The present invention will now be illustrated with reference to the accompanying figures, which are given by way of example only.

FIG. 1b is a top view of the kit shown in FIG. 1a;

FIG. 6 is a top view of a kit for screening for autoantibodies to different parts (epitopes) of TPO;

FIG. 7a is a side view of a kit according to the present invention for screening for fist and second autoantibodies to Tg (autoantibodies Tg-AAb1 and Tg-AAb2);

FIG. 7b is a top view of the kit shown in FIG. 7a;

FIG. 9b is a top view of the kit shown in FIG. 9a; and

DETAILED DESCRIPTION OF THE INVENTION

Figure 1A:
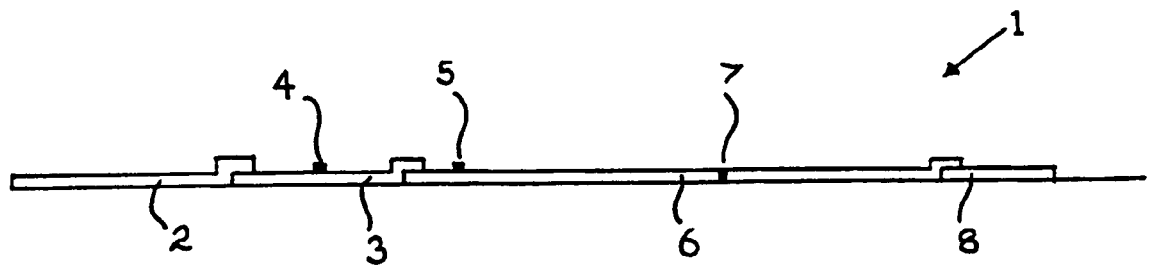
FIG. 1a is a side view of a kit according to the present invention for screening TPO autoantibodies.
Figure 1B:
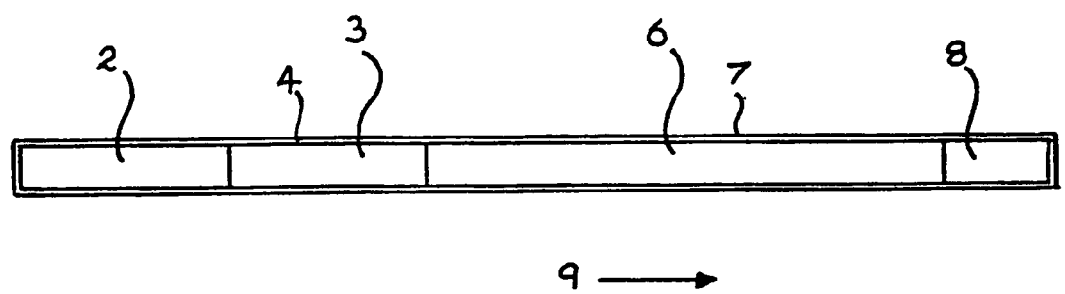

Referring firstly to FIGS. 1a and 1b, there is shown a kit (1) for the screening for autoantibodies to TPO comprising a zone (2) for receiving a sample of body fluid (preferably blood) and includes a cell filter (not shown) for separating red blood cells from the remainder of the blood sample. A pad (3) comprising strepavidin-gold (SA-gold) (4) is adjacent to receiving zone (2). Pad (3) is in communication with a zone comprising TPO-biotin (TPO-bi) (5) which is dried to a nitrocellulose membrane (6). Furthermore, purified antibodies to TPO (7) are immobilised to nitrocellulose membrane (6) and are located downstream from the zone comprising TPO-bi (5). A paper wick (8) is located at an opposite end to receiving zone (2). Wick (8) is designed to permit or potentiate flow from receiving zone (2) towards purified immobilised antibodies to TPO (7).

The following series of steps illustrate the use of kit (1) shown in FIGS. 1a and 1b in a screening method according to the present invention.

Step 1

The first step comprises applying a sample of blood or the like to receiving zone (2). The sample of plasma will then flow towards wick (8).

Step 2

The blood cells are retained in receiving zone (2). The plasma then flows through pad (3) and forms a mixture with SA-gold (4) and this mixture flows towards TPO-bi (5).

Step 3

The plasma-SA-gold mixture arrives at the zone comprising TPO-bi (5) where TPO-bi (5) dissolves allowing formation of a TPO-bi-SA-gold complex. If autoantibodies to TPO are present in the plasma, these will bind to TPO in the TPO-bi-SA-gold complex.

Step 4

The mixture of plasma and TPO-bi-SA-gold complex then flows towards immobilised antibodies to TPO (7).

Step 5

Figure 2A:
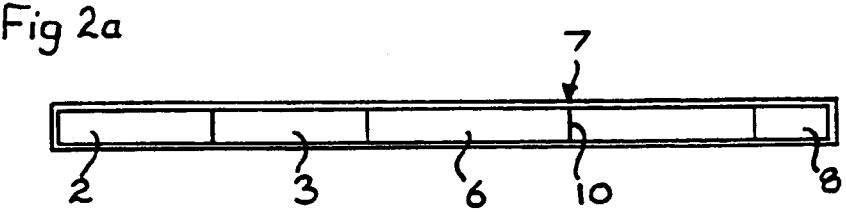
FIGS. 2a and 2b are top views of the kit of FIGS. 1a and 1b and respectively show the results obtained in the absence and presence of autoantibodies to TPO in the sample of body fluid.
Figure 2B:
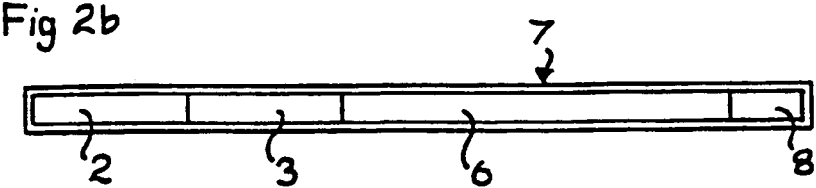

The reaction in the absence of autoantibodies to TPO allows the TPO-bi-SA-gold complex to bind to immobilised antibodies to TPO (7) giving a red-gold line (10), as illustrated in FIG. 2a.

Step 6

The reaction in the presence of autoantibodies to TPO allows autoantibodies to TPO in the plasma to bind to TPO-bi-SA-gold complex preventing the complex from binding to immobilised TPO antibodies (7). Therefore, the absence of a red-gold line at the site of immobilised TPO antibodies (7) indicates the presence of TPO autoantibodies in the sample of body fluid.

Figure 3A:
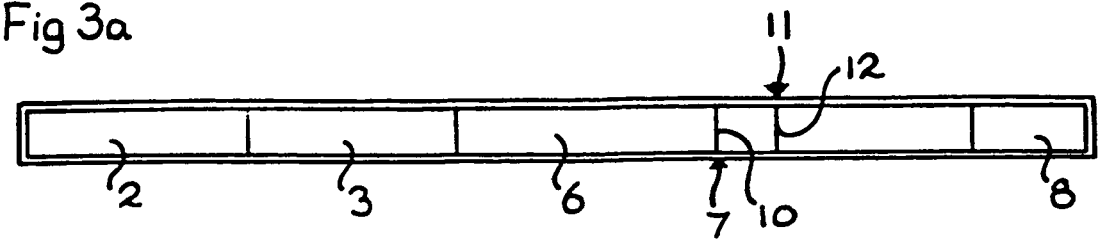
FIGS. 3a and 3b are top views of a kit according to the present invention incorporating a positive control and show the results obtained in the absence and presence of autoantibodies to TPO.

Referring now to FIG. 3a, there can be seen an embodiment of the present invention which is extended to provide a positive control which is stained red irrespective of the presence or absence of TPO autoantibodies. A rabbit antibody (11) to TPO is stained red-gold by a TPO-bi-SA-gold complex giving a red-gold line (12). Therefore, as illustrated, in the absence of autoantibodies to TPO in the sample of body fluid to be tested, immobilised antibodies to TPO (7) are stained red-gold by the TPO-bi-SA-gold complex giving red-gold line (10) (which is also illustrated in FIG. 2a). Therefore, two red-gold lines (10, 12) will be indicative of a sample of body fluid which does not contain autoantibodies to TPO.

Figure 3B:
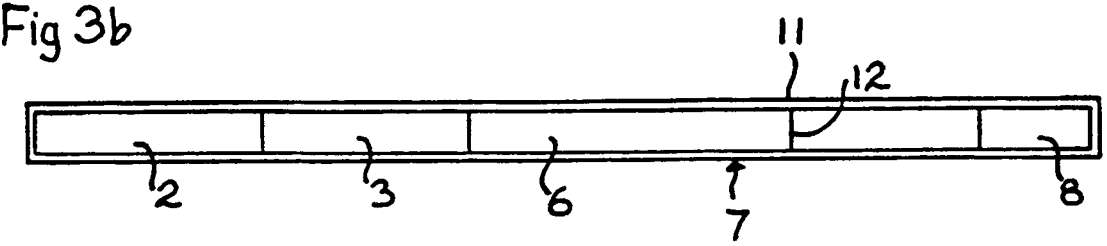

FIG. 3b is identical to FIG. 3a except that it illustrates a reaction where the sample of body fluid to be tested comprises autoantibodies to TPO. In this situation, autoantibodies to TPO in plasma bind to a TPO-bi-SA-gold complex thereby preventing the complex binding to immobilised antibodies to TPO (7). Therefore, in this case, only one red-gold line (for the control) namely line (12), will be visible indicating the presence of TPO autoantibodies in the sample of body fluid.

Figure 4:
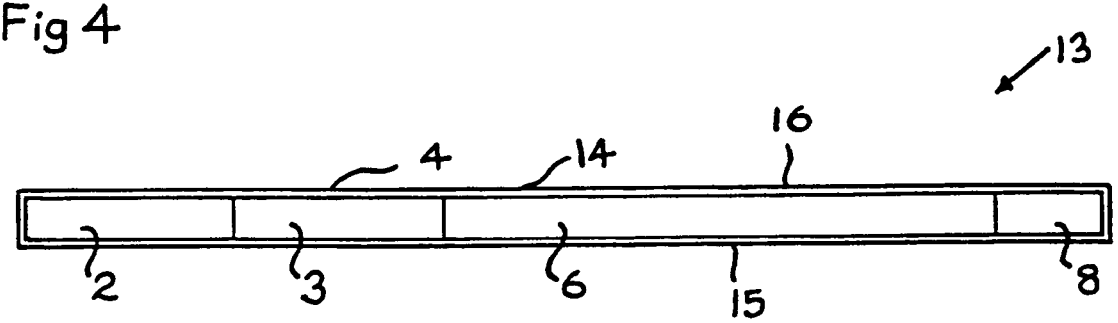
FIG. 4 is a top view of a kit according to the present invention for screening for Tg autoantibodies.

FIG. 4 illustrates a kit (13) for screening for Tg autoantibodies. Kit (13) is identical to kit (1) as shown in FIG. 1, apart from the replacement of TPO-bi with Tg-bi and replacement of the immobilised antibodies to TPO with immobilised antibodies to Tg. More particularly, kit (13) similarly comprises receiving zone (2), pad (3) comprising SA-gold (4) and wick (8). Kit (13) further comprises a zone comprising Tg-bi (14) dried to nitrocellulose membrane (6). Purified antibodies to Tg (15) are immobilised to nitrocellulose membrane (6) and located downstream from Tg-bi (14). An immobilised rabbit antibody to Tg (16) is also present to provide a positive control.

Figure 5:
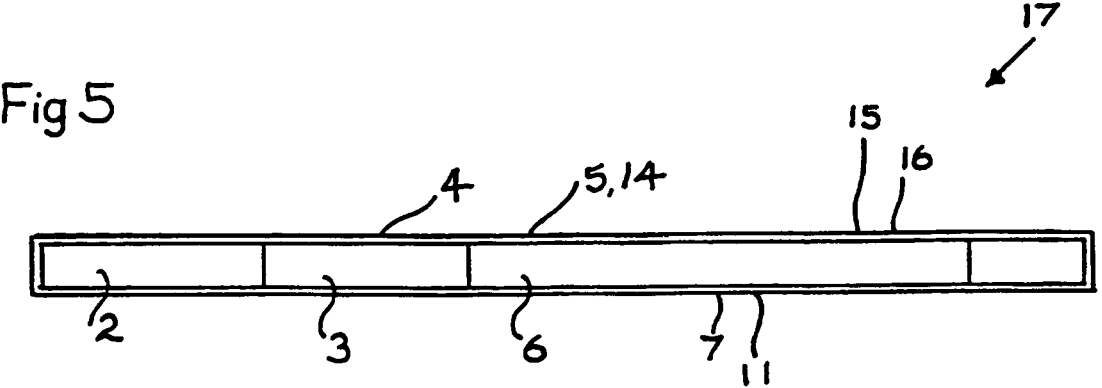
FIG. 5 is a top view of a kit according to the present invention for screening for both Tg autoantibodies and TPb autoantibodies.

FIG. 5 illustrates a single kit (17) for screening for both autoantibodies to TPO and autoantibodies to Tg. More particularly, kit (17) comprises (as previously referred to in kits (1) and (13)) receiving zone (2), pad (3) comprising SA-gold (4) and wick (8). Kit (17) further comprises a zone including both TPO-bi (5) and Tg-bi (14) dried to nitrocellulose membrane (6). Purified antibodies to TPO (7) and purified antibodies to Tg (15) are immobilised to nitrocellulose membrane (6) and are located downstream from TPO-bi (5) and Tg-bi (14). Immobilised rabbit antibodies to TPO (11) and Tg (16) are also present to provide a positive control.

FIG. 6 illustrates a kit (18) for screening for autoantibodies to different parts (first and second epitopes) of TPO. This kit comprises immobilised antibodies to different antigenic epitopes on TPO which are used for the detection of autoantibodies to different parts (first and second epitopes) of TPO. More particularly, kit (18) comprises [as previously referred to in Kits (1), (13) and (17)] receiving zone (2), pad (3) comprises SA-gold (4) and wick (8). TPO-bi (5) is dried to nitrocellulose membrane (6).

TPO antibodies to the first epitope (19) and TPO antibodies to the second epitope (20) are immobilised on nitrocellulose membrane (6). An immobilised rabbit antibody to TPO (11) is also present to provide a positive control.

Referring to FIGS. 7a and 7b, there is shown a kit (21) for screening for first and second autoantibodies to Tg (autoantibodies Tg-AAb1 and Tg-AAb2). As previously referred to in kits (1), (13), (17) and (18), kit (21) comprises zone (2) for receiving a sample of body fluid, pad (3), nitrocellulose membrane (6) and wick (8). Tg-gold (22) is present on pad (3) and is provided adjacent to zone (2). Tg-gold denotes Tg previously labelled with -biotin-antibiotin-colloidal gold and subsequently applied to pad (3).

Purified first and second antibodies (15a, 15b) are immobilised (immobilised antibodies Tg-Ab1 and Tg-Ab2) to nitrocellulose membrane (6) and are located downstream from Tg-gold (22). An immobilised rabbit antibody to Tg (16) is also present to provide a positive control.

Autoantibody Tg-AAb1 binds to the same site of Tg-gold (22) as immobilised Tg-Ab1 (15a). Autoantibody Tg-AAb2 binds to the same site of Tg-gold (22) as immobilised Tg-Ab2 (15b).

The following series of steps illustrate the use of kit (21) shown in FIGS. 7a and 7b in a screening method according to the present invention.

Step 1

The first step comprises applying a sample of blood or the like to receiving zone (2). The sample of plasma will then flow towards wick (8).

Step 2

The blood cells are retained in receiving zone (2). The plasma then flows through pad (3) and forms a mixture with Tg-gold (22) and this mixture flows towards immobilised antibodies Tg-Ab1 and Tg-Ab2 (15a, 15b).

Step 3

The mixture of plasma and Tg-gold (22) reaches immobilised antibodies Tg-Ab1 and Tg-Ab2 (15a, 15b).

Step 4

Figure 8A:
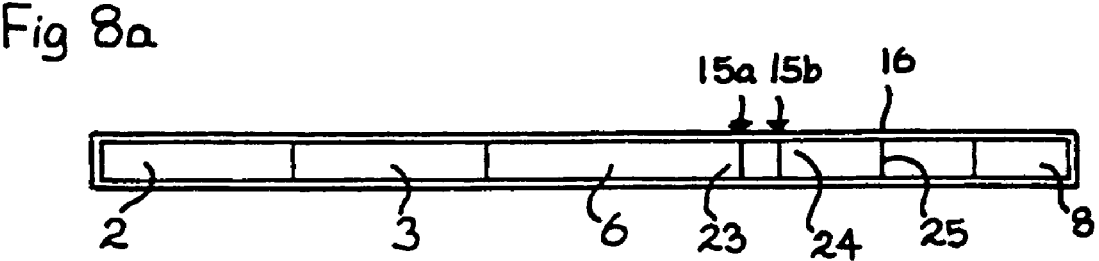
FIGS. 8a, 8b, 8c and 8d are top views of the kit shown in FIGS. 7a and 7b and show the results obtained in the absence and presence of first and/or second autoantibodies to Tg (autoantibodies Tg-AAb1 and Tg-AAb2)

The reaction in the absence of autoantibodies Tg-AAb1 and Tg-AAb2 to Tg in the plasma allows Tg-gold (22) to bind to both immobilised antibodies Tg-Ab1 and Tg-Ab2 (15a, 15b), giving two red gold lines (23, 24) in addition to control line (25) for Tg rabbit antibody (16), as illustrated in FIG. 8a.

Step 5

Figure 8B:
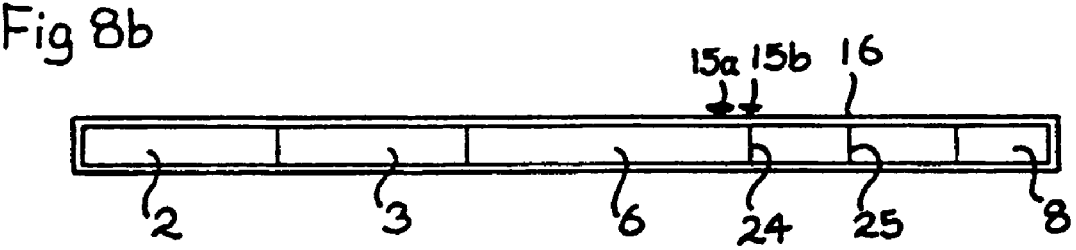

The reaction in the presence of autoantibody Tg-AAb1 to Tg in the plasma allows autoantibody Tg-AAb1 in the plasma to bind to Tg-gold (22) preventing Tg-gold (22) from binding to immobilised antibody Tg-Ab1 (15a). No red gold line is seen at the site of immobilised antibody Tg-Ab1 and indicates the presence of autoantibody Tg-AAb1 to Tg in the plasma. This reaction in the absence of autoantibody Tg-AAb2 to Tg in the plasma allows Tg-gold (22) to bind to immobilised antibody Tg-Ab2 (15b) and a red gold line (24) is seen in addition to control line (25), as illustrated in FIG. 8b.

Step 6

Figure 8C:
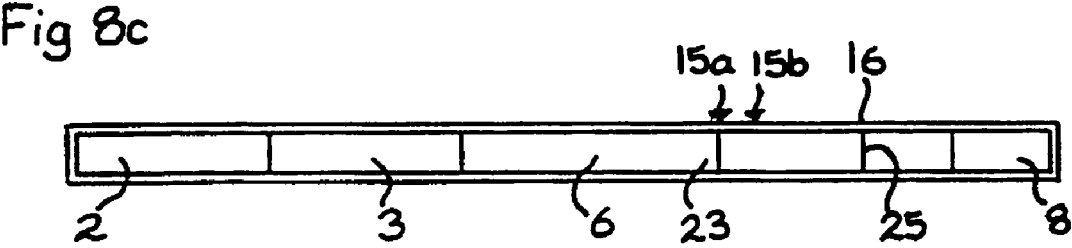

The reaction in the presence of autoantibody Tg-AAb2 to Tg in the plasma allows autoantibody Tg-AAb2 in the plasma to bind to Tg-gold (22) preventing Tg-gold (22) from binding to immobilised antibody Tg-Ab2 (15b). No red gold line is seen at the site of immobilised antibody Tg-Ab2 (15b) and this indicates the presence of autoantibody Tg-AAb2 to Tg in the plasma. This reaction in the absence of autoantibody Tg-AAb1 to Tg in the plasma allows Tg-gold (22) to bind to immobilised antibody Tg-Ab1 (15a) and a red gold line (23) is seen in addition to control line (25), as illustrated in FIG. 8c.

Step 7

Figure 8D:
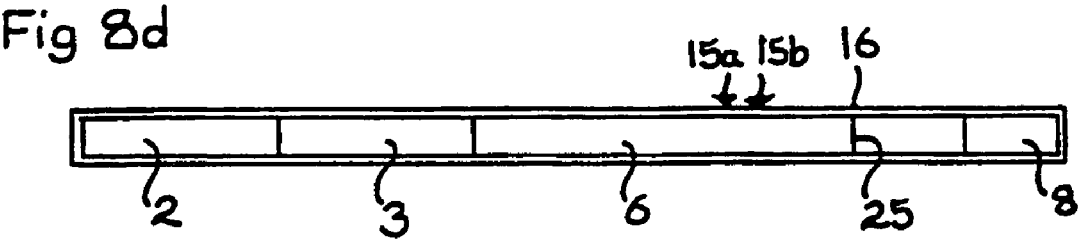

The reaction in the presence of both autoantibodies Tg-AAb1 and Tg-AAb2 to Tg in the plasma allows autoantibodies Tg-AAb1 and Tg-AAb2 in the plasma to bind the Tg-gold (22). Tg-gold (22) is prevented from binding to immobilised antibodies Tg-Ab1 and Tg-Ab2 (15a, 15b). No red gold lines are seen at the sites of immobilised antibodies Tg-Ab1 and Tg-Ab2 (15a, 15b), indicating the presence of autoantibodies Tg-AAb1 and Tg-AAb2 to Tg in the plasma. Red gold control line (25) is seen, as illustrated in FIG. 8d.

Figure 9A:
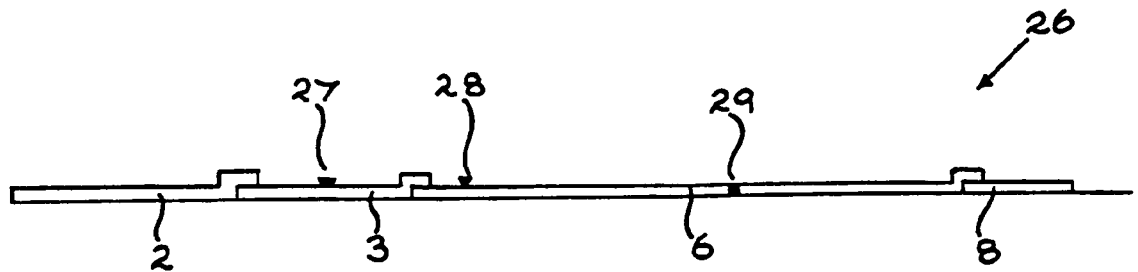
FIG. 9a is a side view of a kit according to the present invention for screening for first and second autoantibodies to TPO (autoantibodies TPO-AAb1 and TPO-AAb2)
Figure 9B:
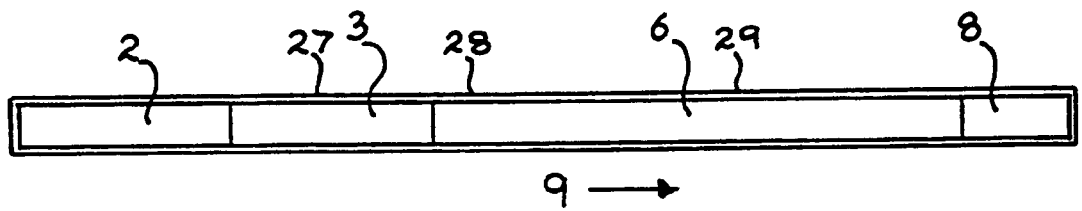

Referring to FIGS. 9a and 9b, there is shown a kit (26) for the screening of first and second autoantibodies to TPO (autoantibodies TPO-AAb1 and TPO-AAb2 respectively). As previously referred to in kits (10), (13), (17), (18) and (21), kit (26) comprises zone (2) for receiving a sample of body fluid, pad (3), nitrocellulose membrane (6) and wick (8). Non-immobilised first antibody to TPO, labelled with colloidal gold, (non-immobilised antibody TPO-Ab1-gold) (27), is provided on pad (3) and is provided adjacent to zone (2). Non-immobilised antibody TPO-Ab1-gold (27) denotes non-immobilised antibody TPO-Ab1 previously labelled with -biotin-antibiotin-colloidal gold and subsequently applied to pad (3). TPO (28) is dried to nitrocellulose membrane (6). Purified second antibody to TPO (29) is immobilised (immobilised antibody TPO-Ab2) to nitrocellulose membrane (6) and is located downstream of non-immobilised antibody TPO-Ab1-gold (27) and TPO (28). Non-immobilised antibody TPO-Ab1-gold binds to the same site of TPO (28) as autoantibody TPO-AAb1. Immobilised antibody TPO-Ab2 binds to the same site of TPO (28) as autoantibody TPO-AAb2.

The following series of steps illustrate the use of kit (26) shown in FIGS. 9a and 9b in a screening method according to the present invention.

Step 1

The first step comprises applying a sample of blood or the like to receiving zone (2). The sample will then flow towards wick (8).

Step 2

The blood cells are retained in receiving zone (2). The plasma then flows through pad (3) and forms a mixture with non-immobilised antibody TPO-Ab1-gold (27) and this mixture flows towards TPO (28).

Step 3

The mixture of step 2 reaches TPO (28) and TPO (28) also dissolves in the mixture.

Step 4

Non-immobilised antibody TPO-Ab1-gold (27) binds with TPO (28) in the mixture, unless autoantibody TPO- AAb1 is present in the plasma. In the presence of autoantibody TPO-AAb1 in the plasma, autoantibody TPO-AAb1 and non-immobilised antibody TPO-Ab1-gold (27) compete for binding with TPO (28) in the mixture.

Step 5

The mixture of plasma, non-immobilised antibody TPO-Ab1 gold (27) and TPO (28) reach immobilised antibody TPO-Ab2 (29).

Step 6

Figure 10A:
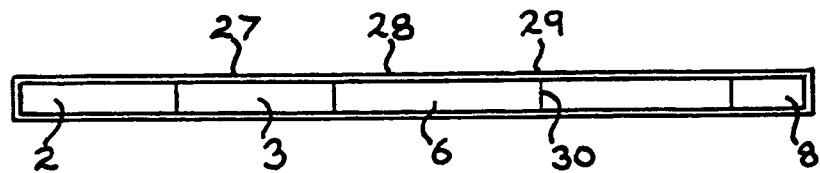
FIGS. 10a and lob are top views of the kit shown in FIGS. 9a and 9b and show the results obtained in the absence and presence of first and/or second autoantibodies TPO (autoantibodies TPO-AAb1 and TPO-AAb2).

The reaction in the absence of autoantibodies TPO-AAb1 and TPO-AAb2 to TPO in the plasma allows TPO (28) to bind to non-immobilised antibody TPO-Ab1-gold (27) and immobilised antibody TPO-Ab2 (29). A red gold line (30) at the location of immobilised antibody TPO-Ab2 (29) indicates the absence of autoantibodies TPO-AAb1 and TPO-AAb2 in the plasma, as illustrated in FIG. 10a.

Step 7

Figure 10B:
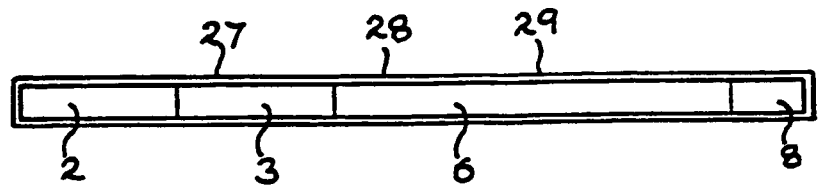

The reaction in the presence of autoantibody TPO-AAb1 and/or autoantibody TPO-AAb2 in the plasma sets up a competition reaction wherein binding of autoantibodies TPO-AAb1 and/or TPO-AAb2 competes with binding of non-immobilised antibody TPO-Ab1-gold (27) and immobilised antibody TPO-Ab2 (29) with TPO (28). In the case where autoantibodies TPO-AAb1 and/or TPO-AAb2 prevent binding of TPO (28) with non-immobilised antibody TPO-Ab1-gold (27) and/or immobilised antibody TPO-Ab2 (29), no red gold line is seen as illustrated in Figure 10b. Alternatively, where competition exists as above in the presence of autoantibodies TPO-AAb1 and TPO-AAb2, there may still be some binding of TPO (28) with non-immobilised antibody TPO-Ab1-gold (27) and immobilised antibody TPO-Ab2 (29), but such binding will be to a lesser extent compared to that of step 6, and a qualitative measure of the quantity of autoantibodies TPO-AAb1 and TPO-AAb2 in the sample will be obtained.

The present invention will now be further illustrated by the following Examples which do not limit the scope of the invention in any way.

EXAMPLE 1

The following tables give the results obtained using a TPO screening kit as shown in FIGS. 1a and 1b and a Tg screening kit as shown in FIG. 4.

TABLE 1

Patient sample results - TPOAb
TPOAb rapid assay

| Patient sample | TPOAb concentration by radioactive assay (U/ml) | Qualitative result by rapid assay |
|---|---|---|
| +TPOAb | | |
| 1 | 165.6 (+) | + |
| 2 | 19.0 (+) | + |
| 3 | 14.6 (+) | + |
| 4 | 56.6 (+) | + |
| 5 | 50.1 (+) | + |
| 6 | 108.7 (+) | + |
| 7 | 171.4 (+) | + |
| 8 | 90.7 (+) | + |
| −TPOAb | | |
| 9 | 0.2 (−) | − |
| 10 | 0.1 (−) | − |

TABLE 1-continued

Patient sample results - TPOAb
TPOAb rapid assay

| Patient sample | TPOAb concentration by radioactive assay (U/ml) | Qualitative result by rapid assay |
|---|---|---|
| 11 | 0.2 (−) | − |
| 12 | 0.2 (−) | − |
| 13 | 0.3 (−) | − |
| 14 | 0.3 (−) | − |

TABLE 2

Patient sample results - TgAb
TgAb rapid assay

| Patient sample | TgAb concentration by radioactive assay (U/ml) | Qualitative result by rapid assay |
|---|---|---|
| +TgAb | | |
| 1 | 52.4 (+) | + |
| 2 | 45.3 (+) | + |
| −TgAb | | |
| 3 | Neg | − |
| 4 | Neg | − |

EXAMPLE 2

This Example describes screening for autoantibodies to Tg using a kit as illustrated in FIGS. 7 and 8.

90 µl of plasma (or sera) or 30 µl of whole blood plus 60 µl of a diluent buffer (150 mM NaCl, 20 mM Tris pH7.6) were used. Results were obtained after 10 minutes. Prior art reference radioactive method was based on that of Beever et al Clinical Chemistry 35 (1989) 1949–954.

TABLE 3

(a) Results obtained in whole blood or plasma obtained from 30 healthy blood donors.

| | plasma (n = 30) | whole blood (Reference method cannot be used with whole blood) |
|---|---|---|
| Tg autoantibody positive by reference radioactive test | 3/30 | — |
| Tg autoantibody positive by a method according to the present invention employing a kit as illustrated in FIGS. 7 and 8 | 3/30 | 1/30 |
| Tg autoantibody negative by reference radioactive test | 27/30 | — |
| Tg autoantibody negative by a method according to the present invention employing a kit as illustrated in FIGS. 7 and 8 | 27/30 | 29/30 |

TABLE 4

(b) Results obtained with sera from patients with systemic lupus erythematosus

|  | Systemic lupus erythematosus |
|---|---|
| Tg autoantibody positive by reference radioactive test | 3/10 |
| Tg autoantibody positive by a method according to the present invention employing a kit as illustrated in FIGS. 7 and 8 | 3/10 |
| Tg autoantibody negative by reference radioactive test | 7/10 |
| Tg autoantibody negative by a method according to the present invention employing a kit as illustrated in FIGS. 7 and 8 | 7/10 |

The above data shows that a method for screening Tg autoantibodies according to the present invention can detect Tg autoantibodies in plasma from healthy blood donors, or sera from patients with systemic lupus erythematosus, at the same prevalence as the reference radioactive test.

EXAMPLE 3

The Example describes screening for autoantibodies to TPO using a kit as illustrated in FIGS. 9 and 10. 90 µl of plasma (or sera) or 30 µl of whole blood plus 60 µl of a diluent buffer (150 mM Nacl; 20 mM Tris pH 7.6) were used. Results were obtained after 10 minutes. Prior art reference radioactive method was based on that of Beever et al Clinical Chemistry 35 (1989) 1949–1954.

TABLE 5

(a) Results obtained in whole blood or plasma obtained from 30 healthy blood donors

|  | plasma | whole blood (reference method cannot be used with whole blood) |
|---|---|---|
| TPO autoantibody positive by reference radioactive test | 3/30 | — |
| TPO autoantibody positive by a method according to the present invention employing a kit as illustrated in FIGS. 9 and 10 | 3/30 | 3/30 |
| TPO autoantibody negative by reference radioactive test | 27/30 | — |
| TPO autoantibody negative by a method according to the present invention employing a kit as illustrated in FIGS. 9 and 10 | 27/30 | 27/30 |

TABLE 6

(b) Results obtained in sera from patients with suspected autoimmune thyroid disease

|  | Suspected autoimmune thyroid disease |
|---|---|
| TPO autoantibody positive by reference radioactive test | 10/13 |
| TPO autoantibody positive by a method according to the present invention employing a kit as illustrated in FIGS. 9 and 10 | 10/13 |
| TPO autoantibody negative by reference radioactive test | 3/13 |
| TPO autoantibody negative by a method according to the present invention employing a kit as illustrated in FIGS. 9 and 10 | 3/13 |

The above data indicates that a method for screening TPO autoantibodies according to the present invention can detect TPO autoantibodies in (a) healthy blood donors or (b) patients suspected of having autoimmune thyroid disease at the same prevalence as the reference radioactive test.

The invention claimed is:

1. A method of detecting in a sample of body fluid the presence of at least one of first and second autoantibodies to at least one antigen, which method comprises:
   (a) providing a first antibody to said antigen, wherein said first antibody is immobilized at a discrete detection position on a substrate and binds a first binding site of said antigen;
   (b) providing a second antibody to said antigen, wherein said second antibody is
      labeled to allow detection of autoantibodies when present in said sample,
      binds a second binding site of said antigen and
      is non-immobilized so that said second antibody flows along said substrate according to step (e);
   (c) providing a source of said at least one antigen, said antigen comprising a first binding site to which either the first autoantibody or the immobilized antibody binds and a second binding site to which either the second autoantibody or the non-immobilized antibody binds;
   (d) contacting said antigen of step (c) with said sample of body fluid and simultaneously or successively said non-immobilized antibody, so as to obtain a mixture wherein said antigen binds with said first and/or second autoantibodies present in said sample of body fluid, and/or said non-immobilized antibody;
   (e) allowing said mixture obtained in step (d) to flow along said substrate of step (a) to said immobilized antibody; and
   (f) monitoring binding of said antigen with either said first and/or second autoantibodies, or said immobilized or non-immobilized antibodies, by detection of the absence or presence of said labeled non-immobilized antibody at said discrete detection position, so as to provide an indication of the presence of said autoantibodies in said sample of body fluid;
   wherein said first and/or second autoantibodies when present in said sample respectively bind with said first and second binding sites of said antigen in step (d) so that respective binding of said immobilized and/or non-immobilized antibodies with said first and second binding sites of said antigen is completely or partially inhibited; and wherein (i) in the absence of said first and second antibodies said labeled non-immobilized antibody is detectable at said discrete detection position on said substrate, or (ii) in the presence of said first and or second autoantibodies said labeled non-immobilized antibodies not detectable at said discrete detection position on said substrate, or is detectable at a reduced level compared to (i).

2. The method according to claim 1, further comprising providing a control which provides a positive signal in the presence or absence of the autoantibody or autoantibodies being screened.

3. The method according to claim 2, wherein said positive control comprises attaching to the substrate at least one control agent that binds to the at least one non-immobilized antibody.

4. The method according to claim 1, wherein said antigen is a thyroid protein.

5. The method according to claim 1, wherein said antigen is thyroid stimulating hormone receptor.

6. The method according to claim 1, wherein said antigen is selected from the group consisting of thyroid peroxidase and thyroglobulin.

7. The method according to claim 1, further comprising screening for the presence of at least one of thyroid stimulating hormone, thyroxine, tri-iodothyronine and thyroglobulin said sample of body fluid.

8. The method according to claim 1, wherein said monitoring comprises observing a colorimetric change dependent on said binding of said autoantibody or autoantibodies with said antigen.

9. The method according to claim 1, wherein said labeling means is colloidal gold.

10. The method according to claim 1, wherein said substrate comprises a membrane of nitrocellulose, cellulose acetate or a polyamide.

11. The method according to claim 1, wherein said substrate comprises an application zone provided upstream of said immobilized antibody on said substrate, and wherein said mixture is allowed to flow from said application zone along said substrate to said immobilized antibody.

12. The method according to claim 11, wherein said application zone contains said source of said antigen, and said mixture is obtained by contacting said sample of body fluid with said antigen in said application zone.

13. The method according to claim 12, wherein said substrate further comprises the non-immobilized second antibody to said antigen, wherein said non-immobilized second antibody is provided downstream of said antigen source in said application zone.

14. A method of screening a sample of body fluid for distinct populations of at least first and second autoantibodies which respectively bind at least first and second distinct antigens, which method comprises:

(a) providing at least first and second antibodies to said at least first and second distinct antigens, wherein said first and second antibodies are immobilized at first and second discrete detection positions on a substrate;

(b) providing one or more sources of said at least first and second distinct antigens, wherein said first antigen comprises a binding site to which either said first autoantibody or said first immobilized antibody binds, and said second antigen comprises a binding site to which either said second autoantibody or said second immobilized antibody binds;

(c) contacting said at least first and second antigens of step (b) with said sample of body fluid, so as to obtain a mixture wherein said first and second antigens respectively bind with said first and/or second autoantibodies when present in said sample of body fluid;

(d) allowing said mixture obtained in step (c) to flow along said substrate of step (a) to said first and second antibodies immobilized at said first and second discrete detection positions on said substrate;

(e) providing labeling means directly or indirectly to said first and second antigens respectively so as to enable the presence of said autoantibodies in said sample of body fluid to be detected; and (f) monitoring binding of said first and second antigens with either said first and/or second autoantibodies, or said immobilized antibodies, by detection of the absence or presence of said directly or indirectly labeled first and second antigens at said first and second discrete detection positions on said substrate, so as to provide an indication of the presence of said autoantibodies in said sample of body fluid, wherein said first and second autoantibodies when present in said sample being screened bind with said first and second antigens when a mixture is obtained in step (c), whereby subsequent respective binding of said first and/or second immobilized antibodies with said first and second antigens in step (d) is completely or partially inhibited;

wherein
(i) in the absence of said first autoantibody said directly or indirectly labeled first antigen is detectable at said first discrete detection position on said substrate; or
(ii) in the presence of said first autoantibody said directly or indirectly labeled first antigen is not detectable at said first discrete detection position on said substrate, or is detectable at said first discrete detection position at a reduced level compared to (i); and wherein
(iii) in the absence of said second autoantibody said directly or indirectly labeled second antigen is detectable at said second discrete detection position on said substrate; or
(iv) in the presence of said second autoantibody said directly or indirectly labeled second antigen is not detectable at said second discrete detection position on said substrate, or is detectable at said second discrete detection position at a reduced level compared to (iii).

15. The method according to claim 14, wherein said labeling means comprise directly labeled first and second antigens.

16. The method according to claim 14, wherein said labeling means comprise first and second non-immobilized labeled antibodies, which respectively bind said first and second antigens at binding sites distinct from the respective binding sites of said first and second antigens for either the autoantibodies being screened, or said immobilized antibodies.

17. The method according to claim 14, further comprising providing a control which provides a positive signal in the presence or absence of the autoantibody or antibodies being screened.

18. The method according to claim 17, wherein the positive control comprises at least one control antibody to at least said first or second antigen, said control antibody being attached to the substrate, wherein said control antibody binds to a site on said first or second antigen distinct from a binding site thereof for the autoantibody being screened.

19. The method according to claim 14, wherein said first and second antigens are distinct thyroid proteins.

20. The method according to claim 14, wherein either said first or second antigen is thyroid stimulating hormone receptor.

21. The method according to claim 14, wherein said first or second antigen is selected from the group consisting of thyroid peroxidase and thyroglobulin.

22. The method according to claim 14, further comprising screening for the presence of at least one of thyroid stimulating hormone, thyroxine, tri-iodothyronine and thyroglobulin in said sample of body fluid.

23. The method according to claim 14, wherein said monitoring comprises observing a colorimetric change dependent on said binding of said first and second autoantibodies with said first and second antigens respectively.

24. The method according to claim 14, wherein said labeling means is colloidal gold.

25. The method according to claim 14, wherein said substrate comprises a membrane of nitrocellulose, cellulose acetate or a polymide.

26. The method according to claim 14, wherein said substrate comprises an application zone provided upstream of said immobilized antibodies on said substrate, and wherein said mixture is allowed to flow from said application zone along said substrate to said immobilized antibodies.

27. The method according to claim 26, wherein said application zone contains said source of first and second antigens, and said mixture is obtained by contacting said sample of body fluid with said first and second antigens in said application zone.

28. The method according to claim 27, wherein said substrate further comprises at least first and second non-immobilized antibodies to said first and second antigens, wherein said non-immobilized antibodies are provided downstream of said antigen source in said application zone.

* * * * *